United States Patent
Lai et al.

(10) Patent No.: US 7,842,000 B2
(45) Date of Patent: Nov. 30, 2010

(54) POSTURE VEST

(75) Inventors: Weichun Lai, Block 402, Bedok North Avenue 3 #12-269, Singapore (SG) 460402; Kangsong Mao, Xinxiang (CN)

(73) Assignees: Kangxu Mao, Xinxiang, Henan Province (CN); Weichun Lai, Singapore (SG)

( * ) Notice: Subject to any disclaimer, the term of this patent is extended or adjusted under 35 U.S.C. 154(b) by 258 days.

(21) Appl. No.: 11/913,692

(22) PCT Filed: May 9, 2006

(86) PCT No.: PCT/SG2006/000156

§ 371 (c)(1),
(2), (4) Date: Nov. 6, 2007

(87) PCT Pub. No.: WO2006/121413

PCT Pub. Date: Nov. 16, 2006

(65) Prior Publication Data

US 2008/0195010 A1    Aug. 14, 2008

(30) Foreign Application Priority Data

May 10, 2005    (CN) .................... 2005 2 0030631 U

(51) Int. Cl.
*A61F 5/00* (2006.01)
(52) U.S. Cl. ..................................... 602/19
(58) Field of Classification Search ................ 602/4–5, 602/19–21, 62–63; 128/845–846, 874–875; 2/216, 305, 311, 312
See application file for complete search history.

(56) References Cited

U.S. PATENT DOCUMENTS

| | | | | |
|---|---|---|---|---|
| 5,235,967 | A | * | 8/1993 | Arbisi et al. ................. 601/101 |
| 6,230,501 | B1 | * | 5/2001 | Bailey et al. ................. 62/51.1 |
| 6,440,094 | B1 | | 8/2002 | Maas |
| 6,709,411 | B1 | * | 3/2004 | Olinger ......................... 602/4 |
| D499,806 | S | | 12/2004 | Machin et al. |
| 2005/0070830 | A1 | | 3/2005 | Schultz |

FOREIGN PATENT DOCUMENTS

| | | |
|---|---|---|
| DE | 19523672 | 11/1995 |
| JP | 09075383 | 3/1997 |
| RU | 2211651 | 9/2003 |
| RU | 2241417 | 12/2004 |

OTHER PUBLICATIONS www.tjbbj.com.
www.doublestar.com.cn.
www.inventionchannel.com/product/product.jsp?productID=102&categoryID=49.
www.supports4less.com/bodyparts/back/.
www.rehaboutlet.com/back_belts.htm.
www.sportabac.co.uk/.../shoulder_brace.html.
www.qiaosi/net/list.asp?id=2429.
www.amazon.com/exec/obidos/tg/detail/-/B0002TUH8O/104-4666208-1636720?v=glance.
www.underworks.com/health/424.html.
www.body-game.com.cn/bljkx.php.

* cited by examiner

*Primary Examiner*—Michael A. Brown
(74) *Attorney, Agent, or Firm*—Volpe and Koenig, P.C.

(57) ABSTRACT

A posture vest for improving body posture has an elastic waist strap; an elastic back strap having a first portion connected to the waist strap; and a pair of length-adjustable elastic shoulder straps connected from a second portion of the back strap to the first portion of the back strap.

21 Claims, 6 Drawing Sheets

POSTURE VEST

FIELD OF INVENTION

The present invention relates to a posture vest and a method for improving body posture.

BACKGROUND

Poor body posture has many harmful effects to one's health, for example, improper sitting posture leads to short reading distance and hence causes or worsens myopia; incorrect sitting posture is also a major root cause for neck pain, neck and shoulder muscle strain, as well as lower back pain. Besides the harms to health, poor body posture is also not desirable for aesthetic reasons, for example, habitual hunchback affects one's mannerism and confidence level. There is, therefore, a need for devices to correct poor body posture.

Poor body posture can be identified by six main conditions, namely, (1) habitual hunchback, (2) round (stooped) shoulders, (3) shoulder imbalance (one shoulder higher than another), (4) scoliosis (abnormal lateral curvature of the spine), (5) habitual forward head position, and (6) habitual lowered head position. Most posture correction devices correct and/or prevent (1) habitual hunchback and/or (2) round shoulders conditions, but very few correction devices correct and/or prevent (3) shoulder imbalance, (4) scoliosis, (5) habitual forward head position, and (6) habitual lowered head position.

Existing posture correction devices typically have structures comprising two elastic shoulder straps and a separate waist strap. The waist strap is fastened firmly around the waist of the wearer. There are generally two groups of designs, one in which non-adjustable elastic shoulder straps connected to a back strap are looped around the shoulders and the back strap is then connected to the waist strap, and another in which length adjustable elastic shoulder straps are stretched around the shoulders from a back strap and attached directly back to the waist strap. However, both design groups have certain shortcomings.

More particularly, designs with non-adjustable elastic shoulder straps do not allow adjustment for custom fitting on the body of individual users. Furthermore, if the two shoulder straps are not separately adjustable, the correction device can only generate outward pulling force to bring stooped shoulders backwards, but fails to generate separately adjustable downward pulling force to correct shoulder imbalance and/or scoliosis.

On the other hand, connecting adjustable elastic shoulder straps directly to the waist strap can result in excessive pulling forces causing the displacement of the waist strap, which subsequently results in loss of overall body posture correcting effect and also causes discomfort to the user.

A need therefore exists to provide a posture vest that addresses at least one of the above-mentioned problems.

SUMMARY

In accordance with an example embodiment of the present invention, there is provided a posture vest for improving body posture comprising: an elastic waist strap; an elastic back strap having a first portion connected to the waist strap; and a pair of length-adjustable elastic shoulder straps connected from a second portion of the back strap to the first portion of the back strap.

Each shoulder strap may be connected to the first portion of the back strap such that a pulling force on the first portion of the back strap is divided into two orthogonal forces.

Each shoulder strap may be connected to the first portion of the back strap such that each shoulder strap is at an angle of about 45° with respect to the waist strap.

The first portion of the back strap may comprise a relief hole for dividing a pulling force on the waist strap into two orthogonal forces.

The shoulder strap may comprise an elastic portion connected to the second portion of the back strap and a length-adjustable non-elastic portion connected to the first portion of the back strap.

The waist strap may be connected from end to end through Velcro.

The waist strap, back strap and shoulder straps may be connected to one another by way of stitch lines.

The posture vest may further comprise at least one heat or cold retaining member.

The posture vest may further comprise at least one massaging member.

The posture vest may further comprise a timer for the massaging member.

The posture vest may further comprise a timer for alerting the wearer to take a rest at predefined intervals.

The posture vest may further comprise at least one pressure sensor for gauging a pressure exerted at a location along the posture vest.

The at least one pressure sensor may be attached to a strip of material extending from the second portion of the back strap towards the neck of the wearer.

The posture vest may further comprise a control unit for alerting the wearer when the pressure exerted at the location is lower than or above a threshold value.

The posture vest may further comprise at least one electrode member for relieving or curing pain and/or alerting the wearer of poor body posture.

The posture vest may further comprise at least one pocket for containing medicine to be placed in contact with the body of the wearer.

The surface of the at least one pocket may be perforated, webbed and/or porous.

The elastic waist strap, the elastic back strap and the pair of length-adjustable elastic shoulder straps may be made of polyester with spandex fabric.

In accordance with another example embodiment of the present invention, there is provided a method for adjusting body posture comprising: providing an elastic waist strap; providing an elastic back strap having a first portion connected to the waist strap; and providing a pair of length-adjustable elastic shoulder straps connected from a second portion of the back strap to the first portion of the back strap.

BRIEF DESCRIPTION OF THE DRAWINGS

Embodiments of the invention will be better understood and readily apparent to one of ordinary skills in the art from the following written description, by way of example only and in conjunction with the drawings, in which.

DETAILED DESCRIPTION

Figure 1:
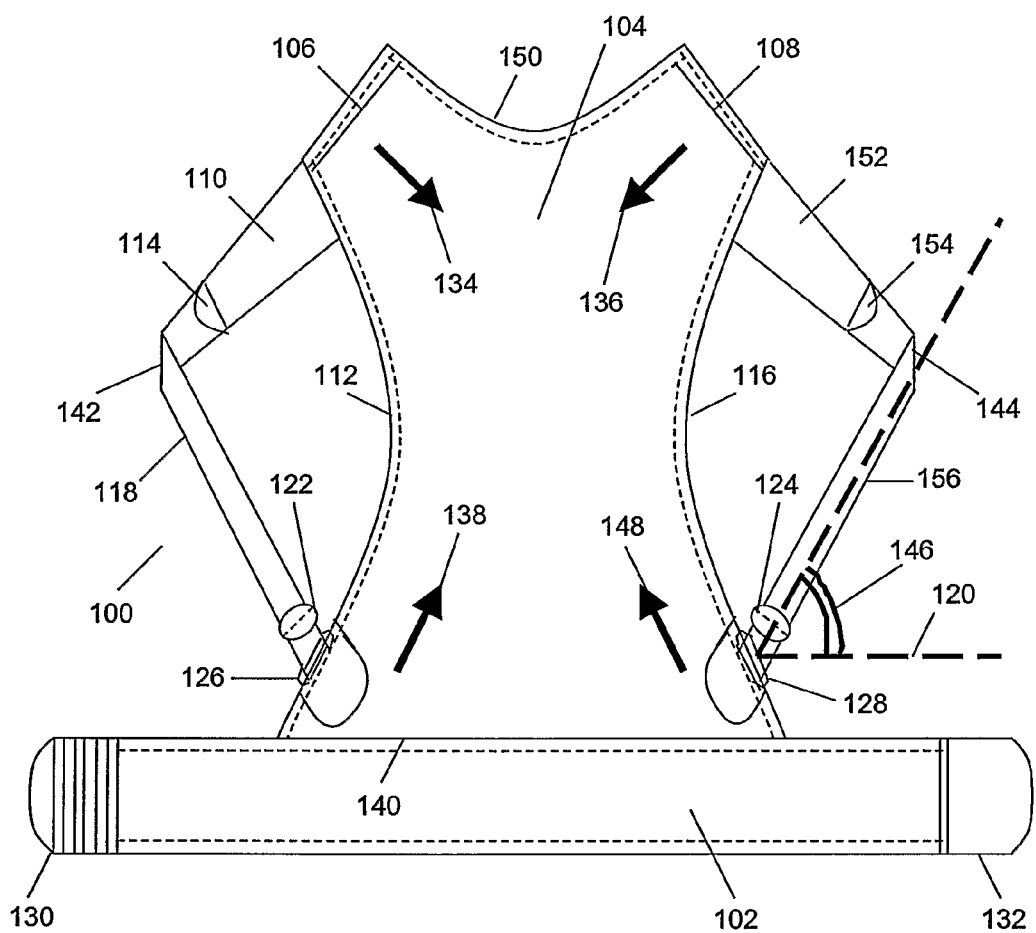
FIG. 1 is a diagram illustrating a posture vest according to a first example embodiment of the present invention.

FIG. 1 shows a posture vest 100 comprising a waist strap 102, a back strap 104 and two shoulder straps 142 and 144. The back strap 104 is connected to the mid section of the waist strap 102 by way of a stitch line 140. The two shoulder straps 142 and 144 are connected to the upper portion of the back strap 104 by way of two respective stitch lines 106 and 108. Each of the shoulder straps 142 and 144 comprises elastic portions 110 and 152, and non-elastic portions 118 and 156 respectively. The elastic portions 110 and 152 of shoulder straps 142 and 144 are connected by way of respective stitch lines 114 and 154 to the non-elastic portions 118 and 156. The non-elastic portion 156 of shoulder strap 144 is permanently attached to the lower portion of the back strap 104 at an angle 146 to the horizontal axis 120. Similarly, the non-elastic portion 118 of shoulder strap 142 is permanently attached to the lower portion of the back strap 104 by the same angle as angle 146 with reference to the same horizontal axis 120. The angle is set at about 45° in the example embodiment. The angle size is determined by the degree of arcing of the arcuate recesses 112 and 116 at the sides of the back strap 104. For conforming to the contours of the neck of a wearer, there is another arcuate recess 150 located at the upper portion of the back strap 104 close to the location of the wearer's neck.

In the example embodiment, the waist strap 102, the elastic portions 110 and 152 of the two shoulder straps 142 and 144, and the back strap 104 are made of highly elastic fabric material with cushioning capabilities to provide comfort to the wearer. In the example embodiment, Polyester with spandex fabric is used. The non-elastic portion of the shoulder straps 118 and 156 are made of non-elastic fabric bands.

The waist strap 102 is an elongated belt with two ends 130 and 132 connectable to each other to form a loop for fitting around the waist section of a wearer. The means for connecting the two ends 130 and 132 can be for example through Velcro, buckles or the like. In the example embodiment, Velcro is used, thus a female Nylon hooks surface 130 is sewn at one end on the waist strap 102 and a male Nylon hooks surface 132 is sewn on the other end of the waist strap 102. One of the surfaces is made longer than the other to allow adjustment of the tension to be exerted around the waist of the wearer. In the example embodiment, the longer surface is the female Nylon hooks surface 130.

The shoulder straps 142 and 144 are wider at the connection to the upper portion of the back strap 104 and taper downward over the shoulders of the wearer to the stitch lines 114 and 154. By being wider at the upper portion of the back strap 104, which is at the wearer's shoulders, the force exerted on the shoulders of the wearer by the shoulder straps 142 and 144, is distributed over a wider surface, thereby providing comfort to the wearer.

The shoulder straps 142 and 144 are permanently attached to the lower portion of the back strap 104 through two respective connector rings 126 and 128. The length of the shoulder straps 142 and 144 are adjustable. The adjustments to the shoulder straps 142 and 144 are made through two mechanical adjusters 122 and 124 respectively. The shorter the length of the shoulder straps 142 and 144, the more reactionary forces caused by stretching of the elastic material of the posture vest 100 are exerted on the wearer to correct the wearer's shoulder positions and overall posture.

In the example embodiment, the non-elastic portions 118 and 156 of the shoulder straps 142 and 144 are advantageously connected to the lower portion of the back strap 104 and not to the waist strap 102. As a result, a vertical pulling force applied to the waist strap 102 is reduced, which in turn reduces the likelihood of upward displacement of the waist strap 102. In addition, the setting of the connection of the non-elastic portions 118 and 156 of the shoulder straps 142 and 144 to the lower portion of the back strap 104 at an angle 146 is to divide the reactionary forces responsible for causing the upward displacement of the waist strap 102 into horizontal and vertical components (i.e. two orthogonal forces) such that the net upward displacement force on the waist strap 102 is further reduced.

The mechanical adjusters 122 and 124, and the connector rings 126 and 128 are located in an accessible position below the shoulders of the wearer to allow easy access for adjustments. The mechanical adjusters 122 and 124, and the connector rings 126 and 128 are not thickset and do not have protrusions that may come into contact with or be felt by the body of the wearer. Therefore, the mechanical adjusters 122 and 124, and the connector rings 126 and 128 do not create any discomfort to the wearer.

The primary function of the mechanical adjusters 122 and 124 is to adjust the tension to be applied over the shoulders by adjusting the length of the shoulder straps 142 and 144 running to the back strap 104 so as to correct and/or prevent round shoulders and habitual hunchback conditions. Furthermore, because the two shoulder straps 142 and 144 are separately adjustable, not only can the posture vest 100 generate outward pulling force to bring stooped shoulders backwards, but can also advantageously generate separately adjustable downward pulling force to correct shoulder imbalance and/or scoliosis.

Another function of the mechanical adjusters 122 and 124 is to adjust the size of the posture vest 100 for fitting the different body sizes of different wearers. It is appreciated that the mechanical adjusters 122 and 124, and connector rings 126 and 128 are made of material such as metal, plastic or the like.

Adjusting the length of the shoulder straps 142 and 144 through mechanical adjusters 122 and 124 increases or decreases two reactionary diagonal backward and downward forces 134 and 136 and two reactionary diagonal upward forces 138 and 148. The shorter the shoulder straps 142 and 144 are, the stronger the reactionary forces 134, 136, 138 and 148 will become.

When the reactionary diagonal backward and downward forces 134 and 136 are increased, a wearer with round shoulder conditions is "forced" to pull back his/her shoulders to the right position, thereby correcting round shoulder problems. At the same time, the vertical component of the reactionary forces 134, 136, 138 and 148 compel the wearer to straighten his/her spine into an upright spinal position, thereby correcting habitual hunchback conditions.

By bringing round shoulders to normal position through backward and downward forces 134 and 136 and bringing crooked spinal cord to normal position through the reactionary forces 134, 136, 138 and 148, the problems of habitual forward head position and habitual lowered head position are also lessened since the head is supported by and connected to the upper portion of the spinal cord.

To correct and/or prevent shoulder imbalance and/or scoliosis, the length of the shoulder straps 142 and 144 shall be separately adjusted, hence to increase or decrease one of the two reactionary diagonal downward forces 134 and 136 accordingly. For example, by reducing the length of the shoulder strap at the higher shoulder side of a wearer and/or increasing the length of another shoulder strap at the lower shoulder side of the wearer, the reactionary diagonal downward force applied to the higher shoulder therefore becomes stronger than the reactionary diagonal downward force on the lower shoulder; hence the higher shoulder tends to be pressed downwards constantly to balance with the lower shoulder. Utilizing the same concept, lateral curvature of the spinal cord can also be corrected and/or prevented by separately adjusting the length of the shoulder straps 142 and 144.

To put on the posture vest 100, the wearer just needs to put his/her hands into the loops formed by the shoulder straps 142 and 144 and the back strap 104. Wearing is simply like putting on a jacket or vest plus securing and tightening the waist strap 102 around the waist of the wearer in the front of the body close to the wearer's navel point. As such, the example embodiment is ergonomically designed for intuitive and comfortable use by the wearer.

Figure 2:
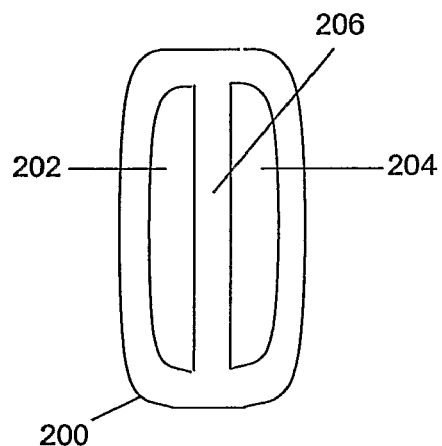
FIG. 2 is a schematic diagram of a mechanical adjuster and connector ring according to one example embodiment of the present invention.

With reference to FIG. 2, the mechanical adjusters 122 and 124 in FIG. 1 each comprise a mechanical adjuster 200. The mechanical adjuster 200 is a flat or round metal frame having a center bar 206 with two adjacent slots 202 and 204 for weaving through the shoulder straps 142 and 144 (in FIG. 1) during shoulder strap length adjustment.

Figure 3:
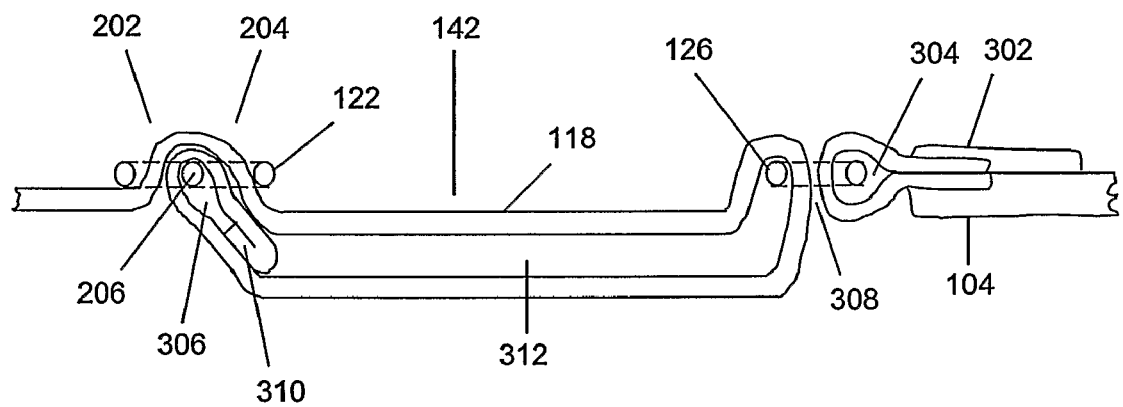
FIG. 3 is a cross-sectional side view of the interconnection of shoulder strap adjustment parts according to one example embodiment of the present invention.

FIG. 3 shows a cross-sectional side view of one shoulder strap 142 illustrating how the non-elastic portion of the shoulder strap 118 is utilised for shoulder strap length adjustment.

Connector ring 126 is permanently attached to a loop 304 formed by a short length of non-elastic fabric band with both ends stitched to the lower portion of the back strap 104. A reinforcement pad 302 is sewn over the loop 304 and the back strap 104 to strengthen the connection of the loop 304 to the back strap 104.

One end of the non-elastic portion 118 of the shoulder strap 142 is permanently attached to the center bar 206 of mechanical adjuster 122 through a loop 306, which is closed by stitching the shoulder strap 142 at a terminating end 310. To enable adjustment, the shoulder strap 142 forms another loop 312 by passing through slot 308 of the connector ring 126 and weaving the shoulder strap 142 through slots 204 and 202 respectively hence overlapping loop 306. Increasing the length of shoulder strap 142 is by pushing and sliding the mechanical adjuster 122 along the shoulder strap 142 towards the connector ring 126. Decreasing the length of the shoulder strap 142 is by pushing and sliding the mechanical adjuster 122 along the shoulder strap 142 away from the connector ring 126.

It is appreciated that the connection of non-elastic portion 118 of the shoulder strap 142 to the back strap 104 can be reversed, that is by having loop 304 and the reinforcement pad 302 sewn over the elastic portion 110 of the shoulder strap 142 and connecting the non-elastic portion 118 of the shoulder strap 142 to the lower portion of the back strap 104 by way of stitch line 114. It is further appreciated that other mechanisms for length adjustment of the shoulder straps 142 and 144 may be implemented, including, but not limited to, tongue buckle bindings with grommets, nylon hooks or the like.

Figure 4:
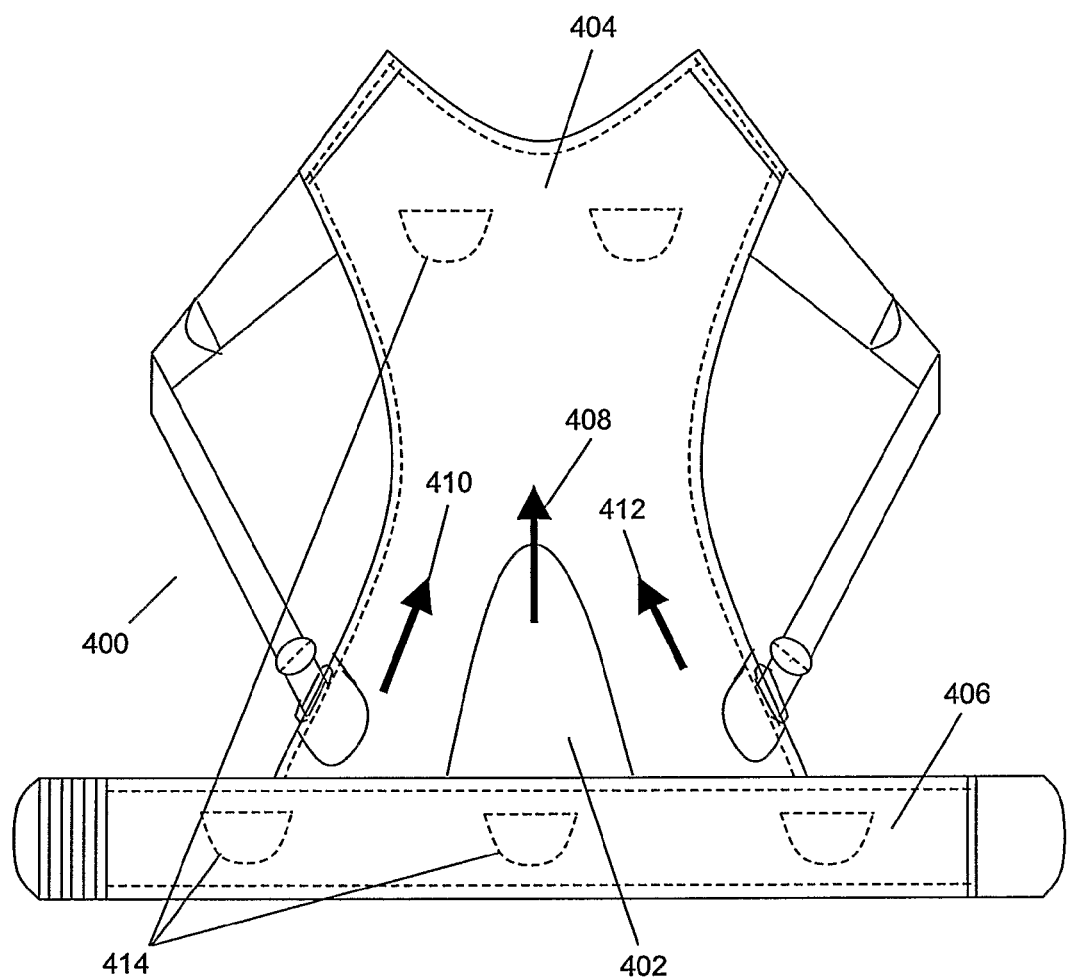
FIG. 4 is a diagram illustrating a posture vest with a relief hole according to a second example embodiment of the present invention.

FIG. 4 shows a posture vest 400 of a second example embodiment of the present invention. The posture vest 400 is similar to the posture vest 100 in FIG. 1 except that posture vest 400 comprises a triangular relief hole 402 located midway at the lower portion of the back strap 404 above the waist strap 406. It is appreciated that the relief hole 402 can be in any shape for example, elliptical, circular, rectangular or the like. The relief hole 402 advantageously further reduces the likelihood of displacement of the waist strap 406 by being pulled in the upward direction above the waist level of a wearer when the wearer performs actions around the waist such as bending the back, sitting down or the like. This is achieved by diverting the upward force 408 that is present in the absence of the relief hole 402 and responsible for upward displacement of the waist strap 406 on the back strap 404 into two diagonal upward forces 410 and 412. This essentially divides the upward force 408 into horizontal and vertical components (i.e. two orthogonal forces). By transferring some forces to horizontal components, the net upward force 408 that is responsible for moving the waist strap 406 upwards is reduced as compared with the example embodiment without the relief hole 402. The resulting effect is the waist strap 406 does not displace upwards due to sudden waist movements by the wearer. The relief hole 402 also makes the waist strap 406 more stretchable and extendable due to lesser elastic material causing reactionary forces to act on the waist strap 406.

The second example embodiment of the present invention may be extended to include pockets 414 that are attached at any location on the inner layer of the posture vest 400, which is in contact with the wearer's body. The pockets 414 can be used to contain herbal medicine, for relieving or curing pain, muscular aches or the like at the body locations of the wearer in contact with the herbal medicine contained in the pockets 414. The surface of the pockets 414 in contact with the wearer's body are webbed, perforated or porous to allow the herbal medicine to come into contact with the wearer's body or seep through the pockets 414 gradually if the herbal medicine is in liquid form.

Figure 5:
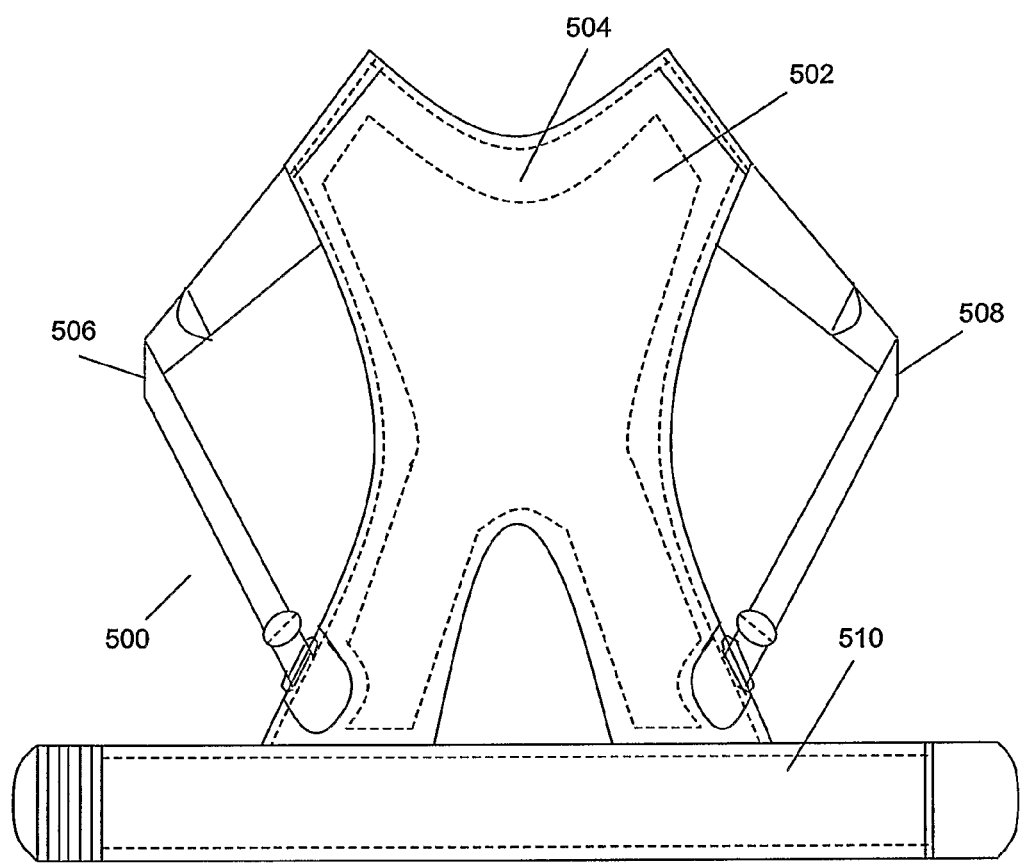
FIG. 5 is a diagram illustrating a posture vest with cold/hot gel pads according to a third example embodiment of the present invention.

FIG. 5 shows a posture vest 500 of a third example embodiment of the present invention. The posture vest 500 is similar to the posture vest 400 in FIG. 4 except that posture vest 500 comprises a piece of heat or cold retaining member such as a cold/hot gel pad 502 attached to the inner layer of the back strap 504. The cold/hot gel pad 502 can retain heat and cold after being exposed under hot or cold environments. Instead of a large single piece of gel pad 502 as shown in FIG. 5, it is appreciated that a few smaller pieces of cold/hot gel pads 502 may be attached to different areas of the inner layer of the back strap 504, shoulder straps 506 and 508, or waist strap 510 of the posture vest 500. It is further appreciated that the cold/hot gel pad 502 may be removable or permanently attached to the back strap 504, shoulder straps 506 and 508, or waist strap 510.

In the case where the gel pad 502 is removable, the gel pad 502 is placed in a refrigerator for cooling before use. When the gel pad 502 is cooled, it can maintain coldness for a significant period of time under room temperature conditions. The applications of the cold gel pad 502 in the posture vest 500 include cooling the wearer and alternatively or additionally help relieve any injury and ailments such as, back pain, shoulder pain, muscle strain or the like.

The cold/hot gel pad 502 may also be placed in the microwave oven for heating up in the case of hot usage. In this case, the gel pad 502 retains the heat absorbed from the heating process by the microwave oven and stays warm under room temperature conditions. The applications of the hot gel pad 502 include providing therapeutic effects to the wearer of the posture vest 500, for example, relieving stomach-ache, aiding healing of injuries or the like, and alternatively or additionally keep the wearer warm.

In the case where the gel pad 502 is permanently incorporated into the posture vest 500, the entire posture vest 500 is placed in the refrigerator or microwave oven for cold or hot usage respectively.

Figure 6:
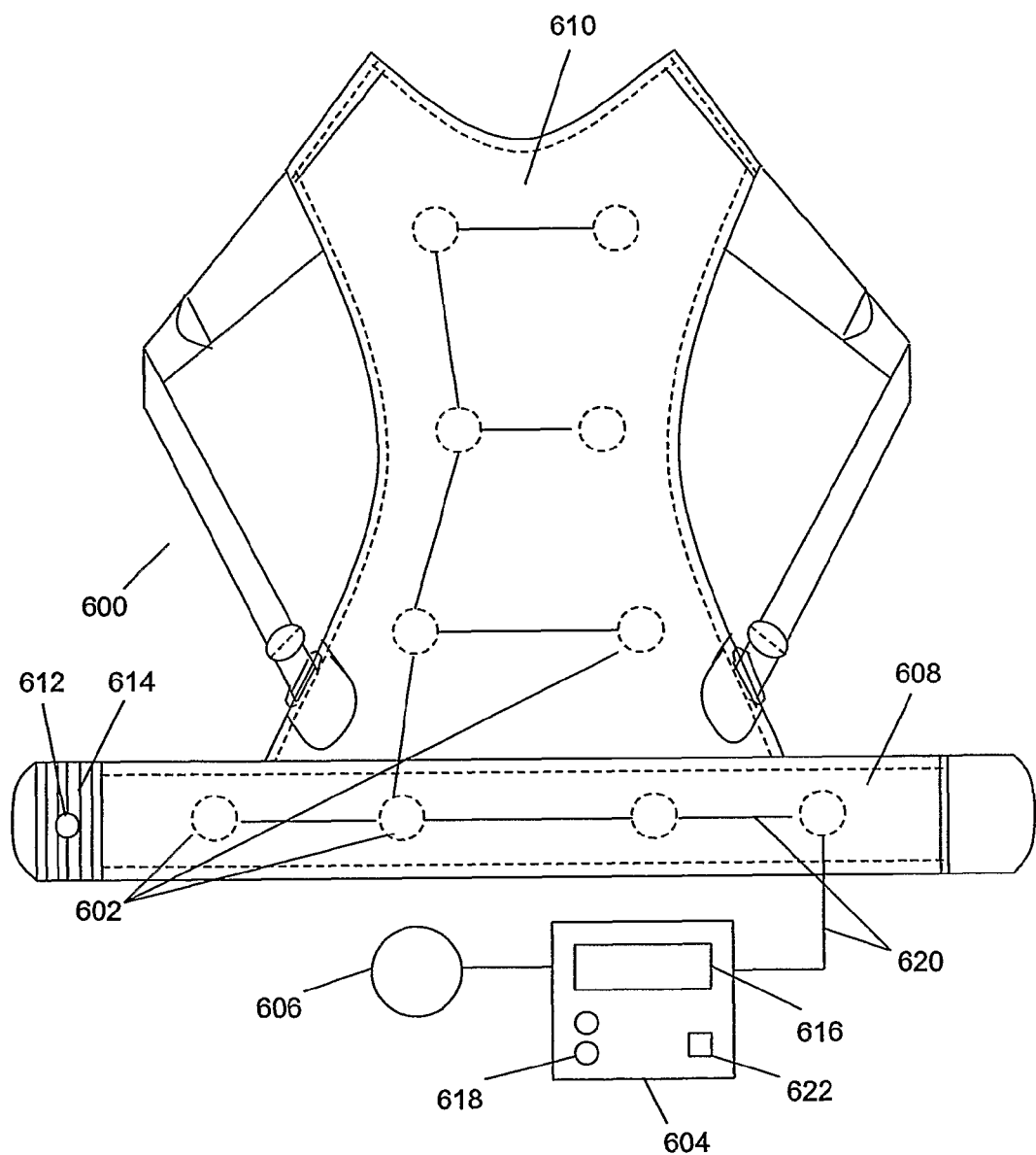
FIG. 6 is a diagram illustrating a posture vest with vibrators (motors) and pockets according to a fourth example embodiment of the present invention.

In a fourth example embodiment, with reference to FIG. 6, massaging members such as vibrators 602 are attached to various locations of a posture vest 600, which is similar to the posture vest 400 in FIG. 4 except for the inclusion of vibrators 602.

One function of the vibrators 602 on the waist strap 608 is to exercise abdominal muscles, hence to enhance the strength of the abdominal muscles of the wearer so that the wearer have enough strength to hold his body straight when not using the posture vest 600. Another function of the vibrators 602 located on the back of the wearer is to relieve back pains caused by poor sitting and/or standing posture through massage.

The vibrators 602 are electric motors with mechanical unbalanced weight (mass) on its driveshaft and the rotating weight will resonate when the motors are switched on. In the current example embodiment, the vibrators 602 are distributed evenly and attached to the inner layers of the waist strap 608 and back strap 610. The vibrators 602 are powered by a power source 606, which can be a Direct Current power supply or an Alternating Current power supply. It is appreciated that the power source 606 may be a battery or a connection to power mains at 240 Volts or 120 Volts or the like.

In the example embodiment, there is an electronic control unit 604 connected through electrical wires 620 to the vibrators 602 and controlling all the vibrators 602. The electronic control unit 604 comprises a display 616 for displaying information relating to the control parameters of the vibrators and buttons 618 for receiving user input. It is appreciated that the display 616 can be a Liquid Crystal Display or the like. It is further appreciated that the electronic control unit 604 and power source 606, in the case where it is a battery, may be incorporated into the posture vest 600 or both incorporated into a separate portable unit.

The electronic control unit 604 controls the intensity of the vibrations of the vibrators 602 and the time duration of the vibrations. The electronic control unit 604 also allows selection of vibrators 602 at selected locations to vibrate. Another function of the electronic control unit 604 is a timer feature, for example, to remind the wearer to take regular breaks when performing near vision tasks. This advantageously prevents the wearer from using his/her eyes continuously without taking a break and acts as a preventive measure against myopia. It is appreciated that the timer feature to remind the wearer to take regular breaks may be controlled by a separate timer unit that is not controlled by the electronic control unit 604. The means for reminding the wearer may be a buzzer 622 that is incorporated into the electronic control unit 604. The buzzer is triggered whenever the preset time is up.

An on/off button 612 is located on the waist strap 608 for switching on the power to the vibrators and electronic control unit 604. In the fourth example embodiment, the button 612 is attached to the female Nylon hooks surface 614, hence, each time the wearer secures the waist strap 608, the button 612 is pressed, and the electronic control unit 604 is switched on. The timer feature for reminding the wearer to take regular breaks may be activated whenever the button 612 is switched on. It is appreciated that the button 612 may be placed at any other location of the posture vest 600 for manual pressing by wearer.

In a fifth example embodiment of the present invention, pressure sensors for correcting and/or preventing habitual forward head position and habitual lower head position are further included in the posture vests described in the previous example embodiments.

Figure 7:
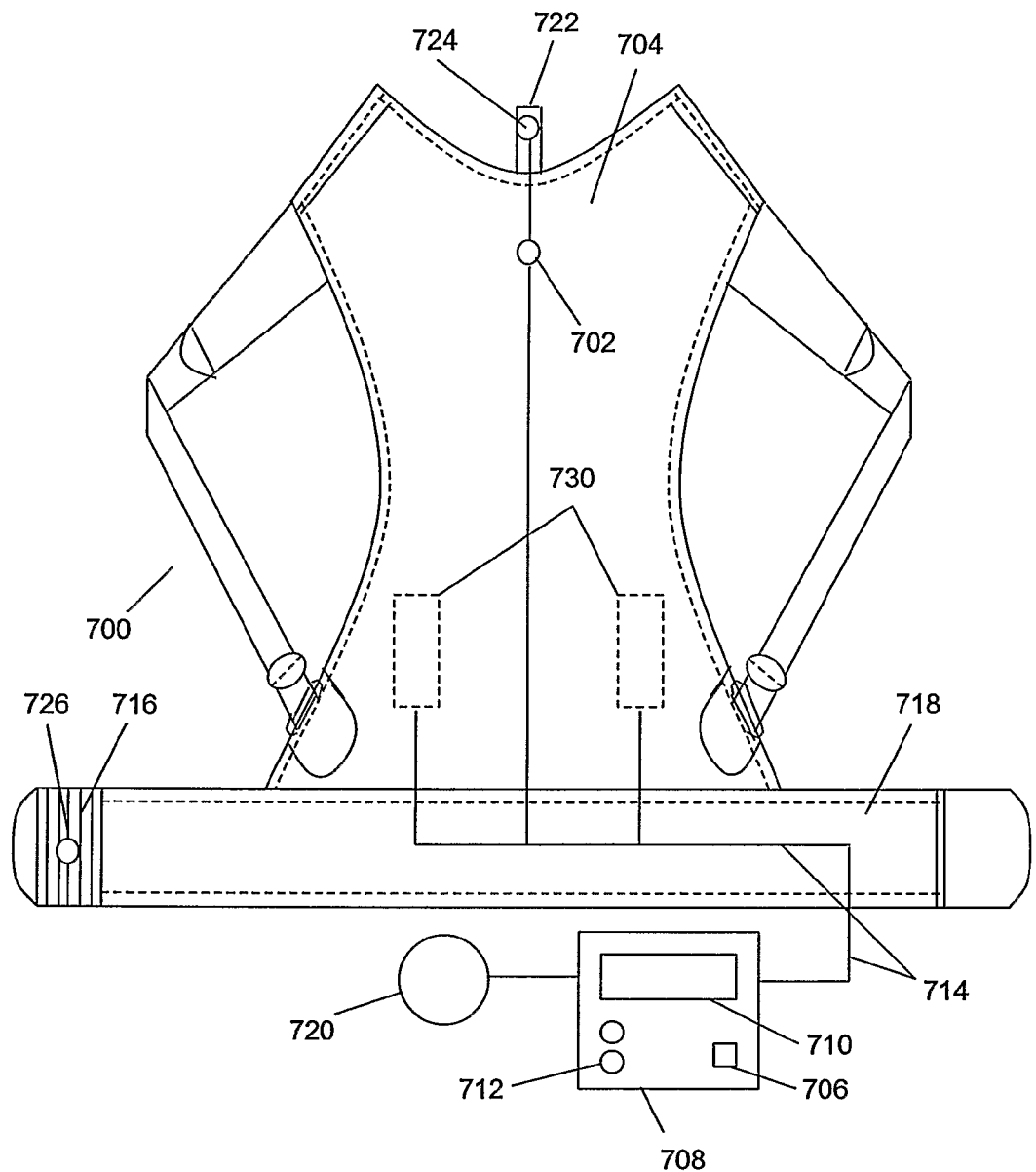
FIG. 7 is a diagram illustrating a posture vest with pressure sensors and electrodes according to a fifth example embodiment of the present invention.

With reference to a posture vest 700 in FIG. 7, a pressure sensor 702 is attached to the upper portion of a back strap 704, which is the location of the upper section of the spinal cord of the wearer. It is appreciated that more than one pressure sensors 702 may be utilised and placed at any position on the posture vest 700 that is capable of detecting variation in pressure caused by the wearer on the posture vest 700 during the habitual forward head position and habitual lower head position.

It is further appreciated that the pressure sensor(s) may be placed beyond the upper portion of the back strap 704 by way of attaching a pressure sensor 724 to a strip of plastic material 722 or the like extending from the upper portion of the back strap 704 towards the direction of the neck of the wearer. Bringing the pressure sensor 724 closer to the neck of the wearer can improve detection of habitual forward head position and habitual lower head position. In a habitual forward head or habitual lower head position, the wearer's neck and upper portion of the spinal cord tends to bend away from a substantially vertical position, which corresponds with a straightened spinal cord. Utilising this fact, the strip of plastic material 722 is disposed in the substantially vertical position such that pressure on the pressure sensor 724 located on the strip of plastic material 722 close to the neck of the wearer is reduced when the wearer's neck bends away from the desirable substantially vertical position. The wearer is warned of the bad posture when the pressure reduces beyond a threshold value.

Before operation, the pressure sensor 702 is preset with a benchmark pressure reading. The benchmark pressure reading is taken when the wearer is in the correct body posture where the ear lobe, shoulders and hip are aligned vertically. In this position, the pressure reading taken when the pressure sensor 702 is pressed between the back strap 704 and the upper section of the spinal cord is set as the benchmark pressure or threshold value. The benchmark pressure reading can be adjusted at any time to customise to each individual or can be set to a predefined value or threshold value based on empirical research data.

During operation, when the wearer lowers or pushes forward his/her head due to a habitual lower head position and/or habitual forward head position condition, the pressure received by the sensor 702 becomes lower than the benchmark pressure. Should the pressure value fall below an unacceptable predefined level, a warning sound may be triggered by a buzzer 706 to remind the wearer of the incorrect head position. Similarly, when the wearer lifts or raises his/her head backward, the pressure received by the sensor 702 becomes higher than the benchmark pressure. Should the pressure value go beyond an unacceptable predefined level, a warning sound may be triggered by the buzzer 706 to remind the wearer of the incorrect head position. In the fifth example embodiment, the buzzer 706 is incorporated into an electronic control unit 708, which controls the buzzer functions. Hence, with the addition of pressure sensors 702, the posture vest 700 can correct and/or prevent not only hunchback and round shoulders, but also habitual lower head position and habitual forward head position.

There is an electronic control unit 708 that is connected to the pressure sensor 702 through electrical wires 714 and is responsible for controlling the pressure sensor 702. The electronic control unit 708 comprises a display 710 for displaying information relating to the control parameters of the pressure sensor 702 such as the pressure readings of the pressure sensor 702 and buttons 712 for receiving user input. It is appreciated that the display 710 can be a Liquid Crystal Display or the like. The electronic control unit 708 is powered by a Direct Current or Alternating Current power supply 720. The power source 720 may be a battery or a connection to power mains at 240 Volts or 120 Volts or the like. It is appreciated that the electronic control unit 708 and power source 720, in the case where it is a battery, may be incorporated into the posture vest 700 or both incorporated into a separate portable unit.

An on/off button 726 is located on the waist strap 718 for switching on the power to the pressure sensor 702 and electronic control unit 708. In the fifth example embodiment, the button 726 is attached to the female Nylon hooks surface 716, hence, each time the wearer secures the waist strap 718, the button 726 is pressed, and the pressure sensor 702 and electronic control unit 708 are switched on. It is appreciated that the button 726 may be placed at any other location of the posture vest 700 for manual pressing by wearer.

It is appreciated that the pressure control features of the electronic control unit 708 in FIG. 7 can be incorporated into the electronic control unit 604 of FIG. 6 if the features of the fourth and fifth example embodiments of the present invention are to be incorporated into one posture vest.

The fifth example embodiment of the present invention may be extended to include electrode members (hereinafter referred to as electrodes) for relieving or curing pain and/or alerting wearers of poor posture. The purpose of the electrodes is to generate electrical stimulation, which is a non-invasive technique that can be used in general treatment of chronic pain, for instance, the common chronic back pain. The electrodes can produce high-frequency stimulation, or acupuncture-like low-frequency, high-amplitude stimulation, or neuromuscular electrical stimulation which utilizes high-intensity electrical stimulation to elicit intermittent contraction and relaxation of proximal muscle fibers and has been widely prescribed for physical rehabilitation and muscle strengthening following surgery and trauma. Electrical stimulation can reduce pain through muscle toning and the prevention of disuse atrophy and muscle degeneration frequently associated with chronic myofascial pain.

With reference to FIG. 7, electrodes 730 are attached to the inner layer of the lower portion of the back strap 704, and connected to the electronic control unit 708 through electrical wire. Stimulation frequency, pulse duration, swing pattern, treatment time can be preset and/or adjusted at the electronic control unit 708 through buttons 712. The wearer of the posture vest 700 can select the desired mode of control through buttons 712 to control the pressure sensors 702 and 724 or the electrodes 730. It is appreciated that the number of electrodes on the posture vest 700 can be any number as much as the posture vest 700 can contain, and the electrodes can be placed at any location on the posture vest 700.

The electrodes 730 utilized in the present example embodiment are Interferential Therapy Electrodes, with carbon silicone self-adhesive. By having the electrodes 730, the posture vest 700 advantageously becomes a Portable Interferential Therapy Electrode unit (Omega™ Inter 4150) for relieving or curing pain for wearers on the move.

The electrodes 730 may work with the pressure sensor 702 and 724 or pressure sensors at other locations of the posture vest 700 to generate electrical simulation automatically and alert or stimulate a wearer to achieve a better posture when a poor body posture is sensed by the pressure sensors through variations in pressure exerted by the wearer on the pressure sensors.

Example embodiments of the present invention may have the following features and advantages.

Example embodiments of the present invention are easy-to-use, user-friendly, ergonomic and comfortable. It also achieves good effect of correcting and/or preventing habitual hunchback, round shoulders, shoulder imbalance, scoliosis, habitual forward head position and habitual lower head position conditions. One major advantage of the example embodiments of the present invention is the prevention of eyesight problems caused by poor sitting posture, which leads to short reading distance, from happening or worsening. Other advantages of the example embodiments of the present invention include but are not limited to relief of back pain, neck and shoulder muscle strain, lower back pain caused by poor sitting and/or standing posture.

Many modifications and other embodiments and setting of different dimensions and shapes can be made to the posture vest and its parts by those skilled in the art having the understanding of the above described disclosure together with the drawings. Therefore, it is to be understood that the device and its utility is not to be limited to the above description contained herein only, and that possible modifications are to be included in the claims of the disclosure.

The invention claimed is:

1. A posture vest for improving body posture comprising:
   an elastic waist strap;
   an elastic back strap having a first portion connected to the waist strap; and
   a pair of length-adjustable elastic shoulder straps connected from a second portion of the back strap directly to the first portion of the back strap.

2. A posture vest as claimed in claim 1, wherein each shoulder strap is connected to the first portion of the back strap such that a pulling force on the first portion of the back strap is divided into two orthogonal forces.

3. A posture vest as claimed in claim 1, wherein each shoulder strap is connected to the first portion of the back strap such that each shoulder strap is at an angle of about 45° with respect to the waist strap.

4. A posture vest as claimed in claim 1, wherein the first portion of the back strap comprises a relief hole for dividing a pulling force on the waist strap into two orthogonal forces.

5. A posture vest as claimed in claim 1, wherein the shoulder strap comprises an elastic portion connected to the second portion of the back strap and a length-adjustable non-elastic portion connected to the first portion of the back strap.

6. A posture vest as claimed in claim 1, wherein the waist strap is connected from end to end through Velcro.

7. A posture vest as claimed in claim 1, wherein the waist strap, back strap and shoulder straps are connected to one another by way of stitch lines.

8. A posture vest as claimed in claim 1, further comprising:
   at least one heat or cold retaining member.

9. A posture vest as claimed in claim 1, further comprising:
   at least one massaging member.

10. A posture vest as claimed in claim 9 further comprising:
    a timer for the massaging member.

11. A posture vest as claimed in claim 1, further comprising:
    a timer for alerting the wearer to take a rest at predefined intervals.

12. A posture vest as claimed in claim 1, further comprising:

at least one pressure sensor for gauging a pressure exerted at a location along the posture vest.

13. A posture vest as claimed in claim 12, wherein the at least one pressure sensor is attached to a strip of material extending from the second portion of the back strap towards the neck of the wearer.

14. A posture vest as claimed in claim 12, further comprising:
- a control unit for alerting the wearer when the pressure exerted at the location is lower than or above a threshold value.

15. A posture vest as claimed in claim 1, further comprising:
- at least one electrode member for relieving or curing pain and/or alerting the wearer of poor body posture.

16. A posture vest as claimed in claim 1, further comprising:
- at least one pocket for containing medicine to be placed in contact with the body of the wearer.

17. A posture vest as claimed in claim 16, wherein the surface of the at least one pocket is perforated, webbed and/or porous.

18. A posture vest as claimed in claim 1, wherein the elastic waist strap, the elastic back strap and the pair of length-adjustable elastic shoulder straps are made of polyester with spandex fabric.

19. A posture vest as claimed in claim 1, wherein each of said length-adjustable elastic shoulder straps forms a separate loop to receive a respective arm of a wearer, such that adjusting each of said length-adjustable elastic shoulder straps provides a diagonal backward and downward force on said wearer's shoulders to assist in correcting said wearer's posture.

20. A method for adjusting body posture comprising:

providing an elastic waist strap;

providing an elastic back strap having a first portion connected to the waist strap; and providing a pair of length-adjustable elastic shoulder straps connected from a second portion of the back strap directly to the first portion of the back strap.

21. A method for adjusting body posture as claimed in claim 20, further comprising:
- inserting an arm of a wearer through a loop formed by each of said length-adjustable elastic shoulder straps; and
- adjusting each of said length-adjustable elastic shoulder straps to provide a diagonal backward and downward force on said wearer's shoulders to assist in correcting said wearer's posture.

* * * * *